(12) United States Patent
Antoniazzi

(10) Patent No.: US 9,210,784 B2
(45) Date of Patent: Dec. 8, 2015

(54) SHADE STRUCTURE

(71) Applicant: Marco Antoniazzi, Treviso (IT)

(72) Inventor: Marco Antoniazzi, Treviso (IT)

( * ) Notice: Subject to any disclaimer, the term of this patent is extended or adjusted under 35 U.S.C. 154(b) by 0 days.

(21) Appl. No.: 14/448,368

(22) Filed: Jul. 31, 2014

(65) Prior Publication Data
US 2015/0034843 A1 Feb. 5, 2015

(30) Foreign Application Priority Data

Aug. 1, 2013 (IT) .......................... TV2013U0035 U

(51) Int. Cl.
*A61L 2/10* (2006.01)
*H05G 2/00* (2006.01)
*E06B 9/42* (2006.01)

(52) U.S. Cl.
CPC .. *H05G 2/00* (2013.01); *A61L 2/10* (2013.01); *E06B 9/42* (2013.01)

(58) Field of Classification Search
CPC ....... A61L 2/00; A61L 2/0029; A61L 2/0035; A61L 2/0041; A61L 2/0047; A61L 2/0052; A61L 2/0058; A61L 9/16; A61L 9/18; A61L 9/20
USPC ............. 250/453.11, 454.11, 455.11; 422/22, 422/23, 24
See application file for complete search history.

(56) References Cited

U.S. PATENT DOCUMENTS

| | | | |
|---|---|---|---|
| 6,168,291 B1 * | 1/2001 | Rockey | F21V 14/08 362/278 |
| 2002/0079063 A1 | 6/2002 | Sheward | |
| 2006/0076113 A1 | 4/2006 | Park | |
| 2010/0218431 A1 | 9/2010 | Hardison, III et al. | |
| 2010/0320399 A1 * | 12/2010 | Speer | B65B 55/08 250/491.1 |
| 2012/0132374 A1 | 5/2012 | Lee | |

FOREIGN PATENT DOCUMENTS

| | | |
|---|---|---|
| CN | 202582005 U | 12/2012 |
| DE | 102004049336 A1 | 4/2006 |
| DE | 19655307 B4 | 5/2008 |
| GB | 1162959 A | 9/1969 |
| KR | 20110031810 A | 3/2011 |
| WO | 2010136917 A1 | 12/2010 |

OTHER PUBLICATIONS

International Search Report and Written Opinion issued Sep. 25, 2014 re: Application No. PCT/EP2014/065967.

* cited by examiner

*Primary Examiner* — Nicole Ippolito

(74) *Attorney, Agent, or Firm* — Cantor Colburn LLP

(57) ABSTRACT

A shade structure comprising a horizontal box that is open in a lower region and comprises within it a motorized roller with a shade associated therewith, cooperating with optional guides, and at least one bactericidal lamp.

11 Claims, 5 Drawing Sheets

SHADE STRUCTURE

The present invention relates to a shade structure.

BACKGROUND OF THE INVENTION

Nowadays it is known to provide shades that can for example be at one end slideably associated with a pole in order to be able to make them slide transversely for example to a window, or they can be wound at a motorized roller that enables automatic descent and ascent.

A problem that nowadays is found in the known art consists of the scant hygiene of shades, which periodically have to be taken down in order to be subjected to washing and then put back up in place.

Furthermore it has been found to be impossible to use conventional shades in particular environments, such as for example hospitals or clinics or medical studies or gyms, given that, in addition to having dust deposited on them, they become fertile ground for the proliferation of bacteria.

SUMMARY OF THE INVENTION

The aim of the present application is therefore to solve the above mentioned technical problems, by eliminating the drawbacks in the cited known art and hence providing a shade that can be employed even in special environments in which a high degree of sanitary hygiene is required.

Within this aim, an object of the invention is to provide a shade whose use can be protracted over time, thus dispensing with the need to carry out continual and periodic washing of the shade proper.

Another object of the invention is to provide an invention that makes it possible to maintain the shade, even if not used, in conditions of utmost sanitary hygiene.

Another object is to provide an invention that is structurally simple and low cost and can be made with the usual conventional plants.

This aim and these and other objects which will become better apparent hereinafter are achieved by a shade structure, characterized in that it comprises a horizontal box that is open in a lower region and comprises within it a motorized roller with a shade associated therewith, cooperating with optional guides, and at least one bactericidal lamp.

BRIEF DESCRIPTION OF THE DRAWINGS

Further characteristics and advantages of the invention will become better apparent from the detailed description of a particular, but not exclusive, embodiment, illustrated by way of non-limiting example in the accompanying drawings wherein.

DESCRIPTION OF THE PREFERRED EMBODIMENTS

Figure 1:
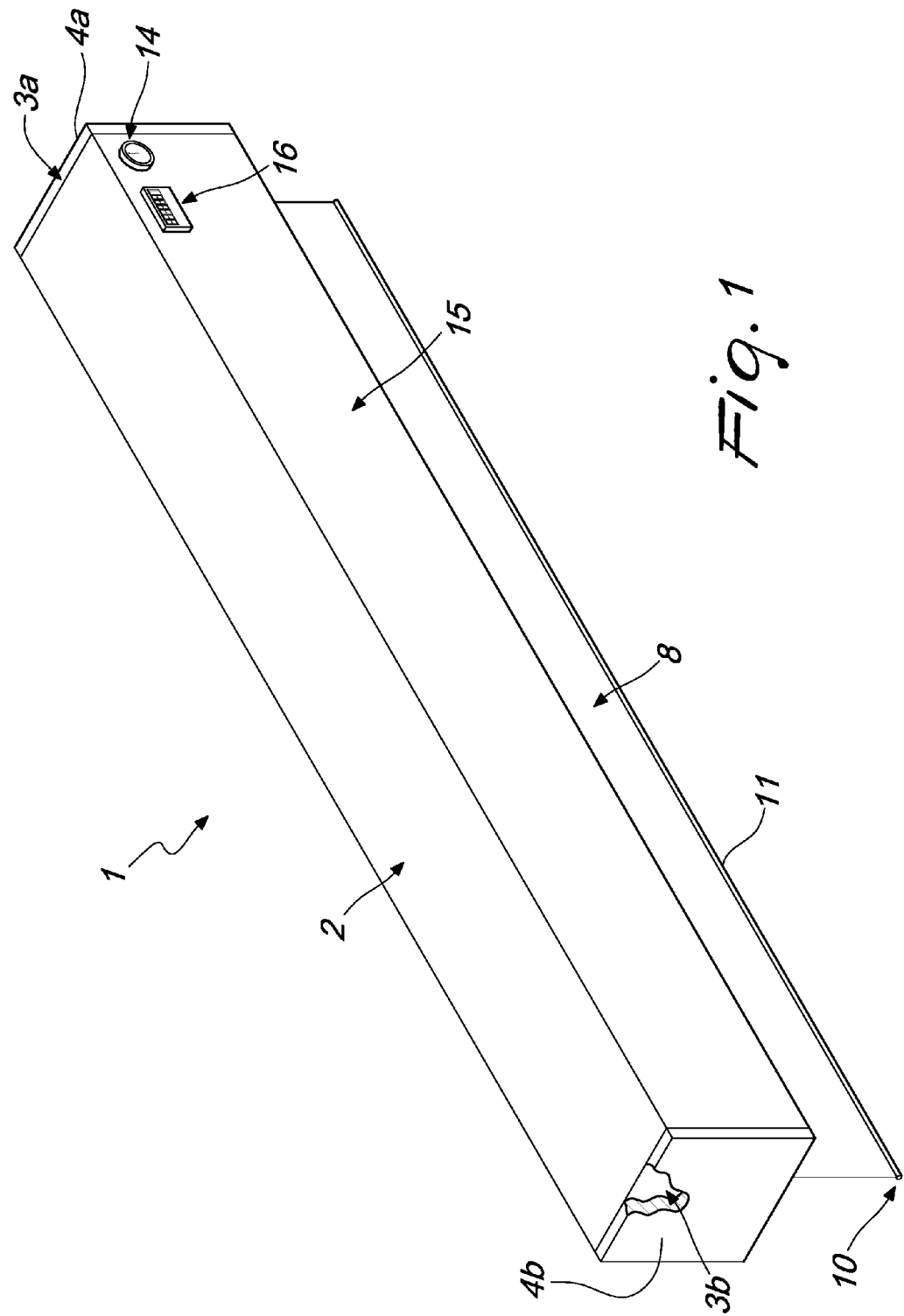
FIG. 1 is a perspective view of the structure with the shade partially lowered.
Figure 2:
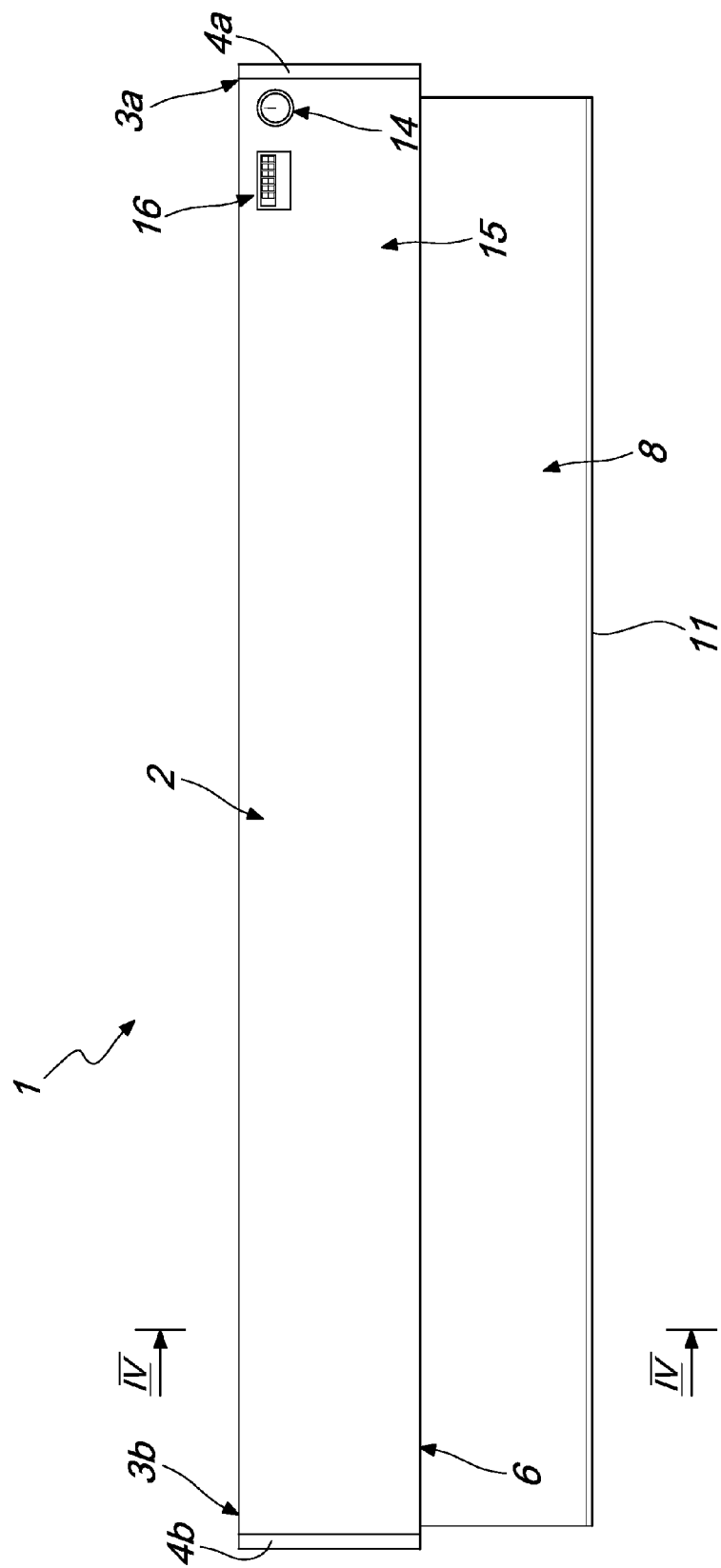
FIG. 2 is a front elevation view of the shade structure.
Figure 3:
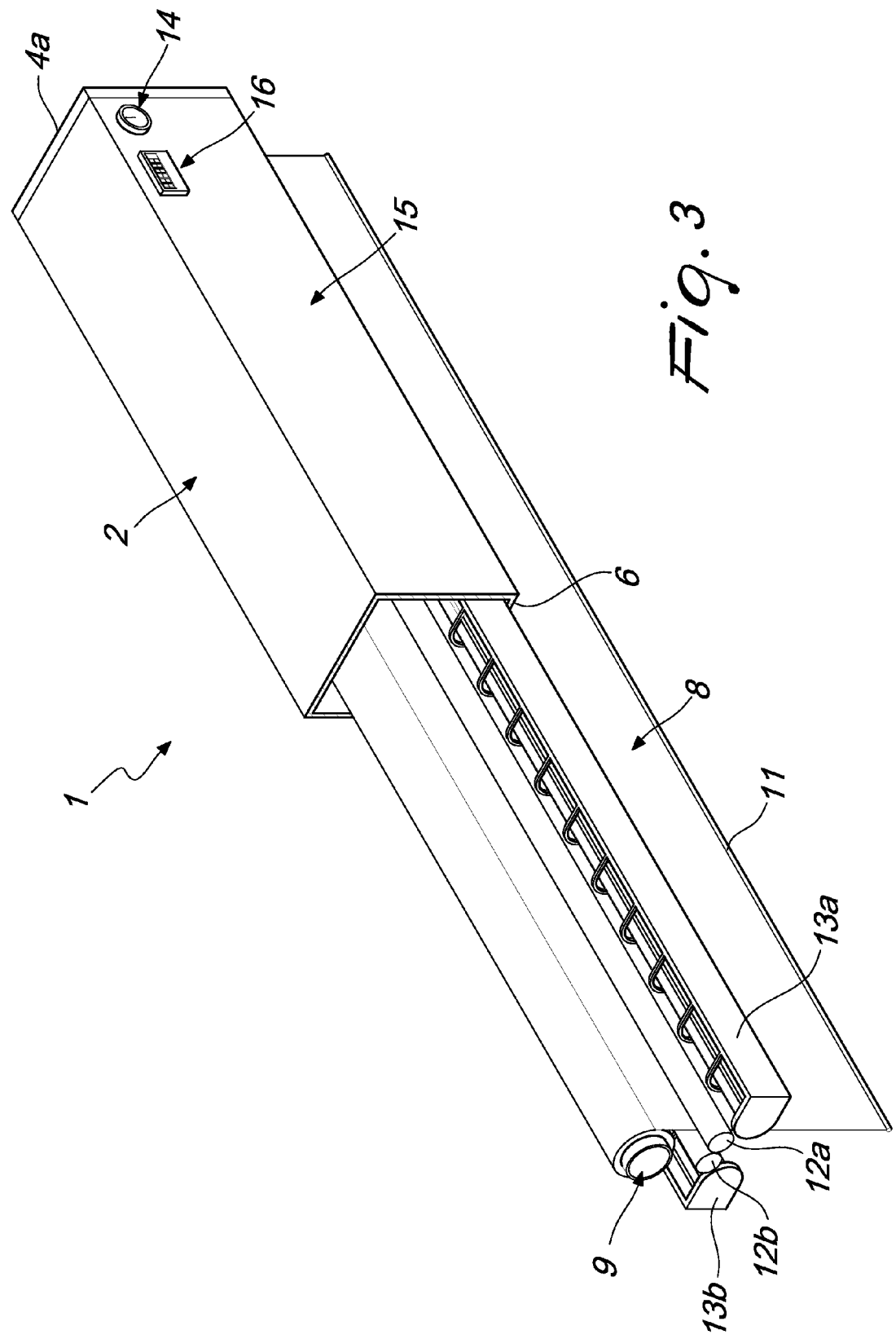
FIG. 3 is a perspective view of the shade structure with the box partially cut away.
Figure 4:
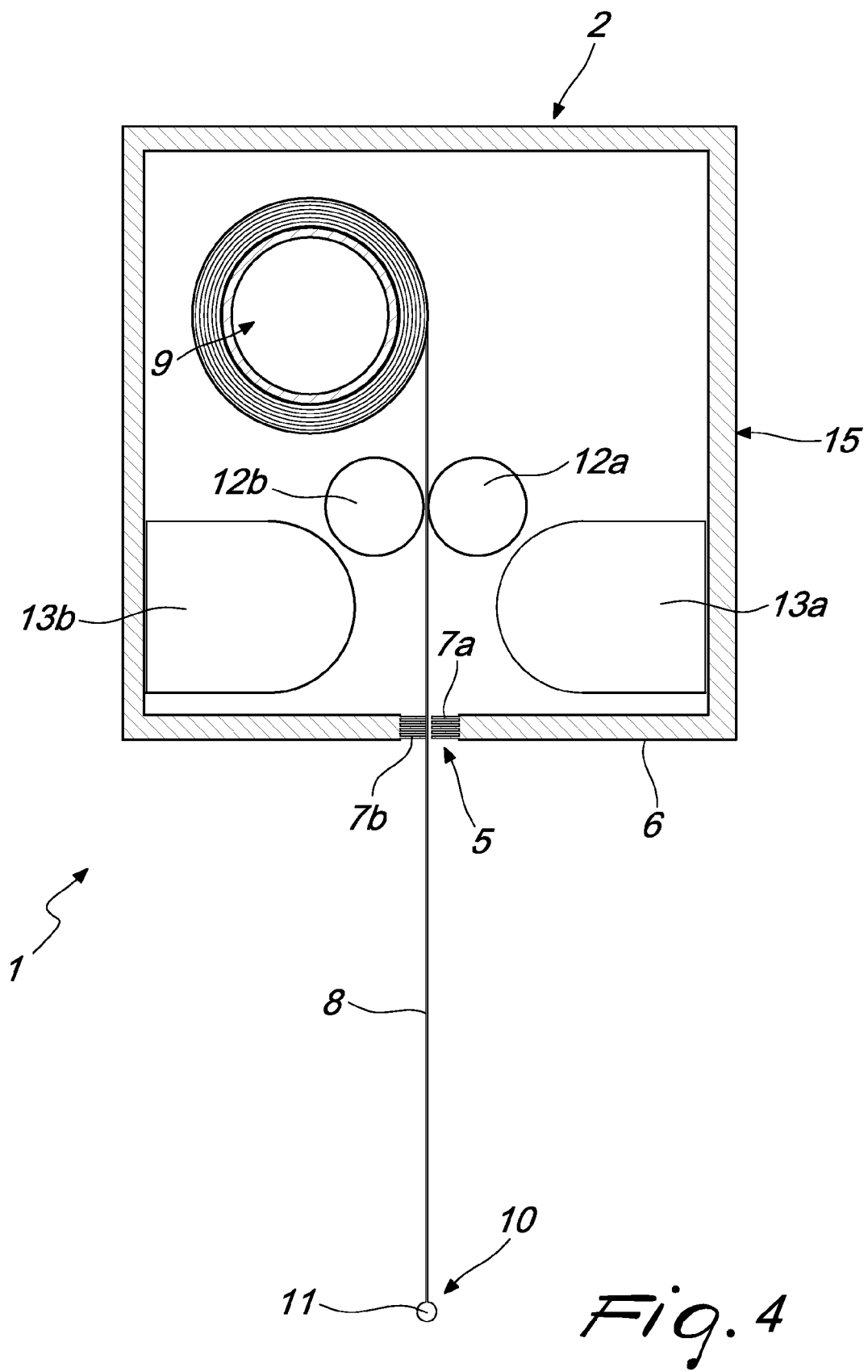
FIG. 4 is a cross-section taken along the line IV-IV in FIG. 2.

In the embodiments illustrated, individual characteristics shown in relation to specific examples may in reality be interchanged with other, different characteristics, existing in other embodiments.

With reference to the figures, the reference numeral 1 generally designates a shade structure that is constituted by a horizontal box 2, made of metal or of plastic material or of a composite material, which preferably has a transverse cross-section that is polygonal in plan, preferably square.

The box 2 has open ends 3a, 3b which can be closed by way of adapted covers 4a, 4b; moreover, an opening 5 is also present at a central region of the underside 6.

The opening 5 is partially closed by a pair of brushes 7a, 7b which are arranged mutually opposite so as to allow the passage between them of a shade 8.

The shade is advantageously made with a fire-retardant fabric that can also be optionally chemically treated to close the fibers and make it water-repellent so as to prevent dirt from penetrating inside it.

Advantageously the shade 8 has a weight that is variable between 250-300 g/m$^2$.

The function of the pair of brushes 7a, 7b is to keep out dust.

Inside the box 2 a roller 9 is provided, which is motorized and advantageously arranged in a region that lies above and offset with respect to the pair of brushes 7a, 7b.

The roller 9 is advantageously constituted by an aluminum tube and is moved by way of an adapted axial motor, optionally removable.

The shade 8 is wound around the roller 9 and its end 10 is advantageously associated with a counterweight 11.

In the intermediate region between the roller 9 and the pair of brushes 7a, 7b, a pair of guides 12a, 12b is advantageously arranged, between which the shade 8 is made to slide.

The function of the pair of guides 12a, 12b is to guide the correct positioning of the shade 8 at the underlying opening 5.

Arranged inside the box 2 a pair of bactericidal lamps 13a, 13b are provided, which are arranged mutually opposite in a region that is adjacent to the underside 6 of the box 2.

Advantageously the pair of bactericidal lamps 13a, 13b is arranged in a region underlying the pair of guides 12a and 12b, such that the shade 8 is positioned between them in a condition substantially perpendicular to the axis of the pair of lamps.

The pair of bactericidal lamps 13a, 13b is preferably of the type with UV-C rays, for example the UV DIRECT E75H-H model of the Light Progress company, which disinfects the fabric.

Advantageously the pair of bactericidal lamps 13a, 13b is activated together with the motor of the roller 9 while it raises and lowers the shade 8.

Another function of the pair of brushes 7a, 7b is to prevent the rays of the lamps from emanating outside the box 2.

Also advantageously present is a lapsed time meter 14 which is arranged on the front surface 15 of the box 2.

Also advantageously present, again on the front surface 15, is an on/off indicator 16 the function of which is to display whether the lamps are in operation.

Thus it has been found that the invention fully achieves the intended aim and objects, a shade structure having been obtained which can also be used in special environments in which a high level of sanitary hygiene is required, the shade being sanitized at each use and kept in the box when not in use.

Obviously the materials used as well as the dimensions of the individual components of the invention may be more relevant according to specific requirements.

Figure 5:
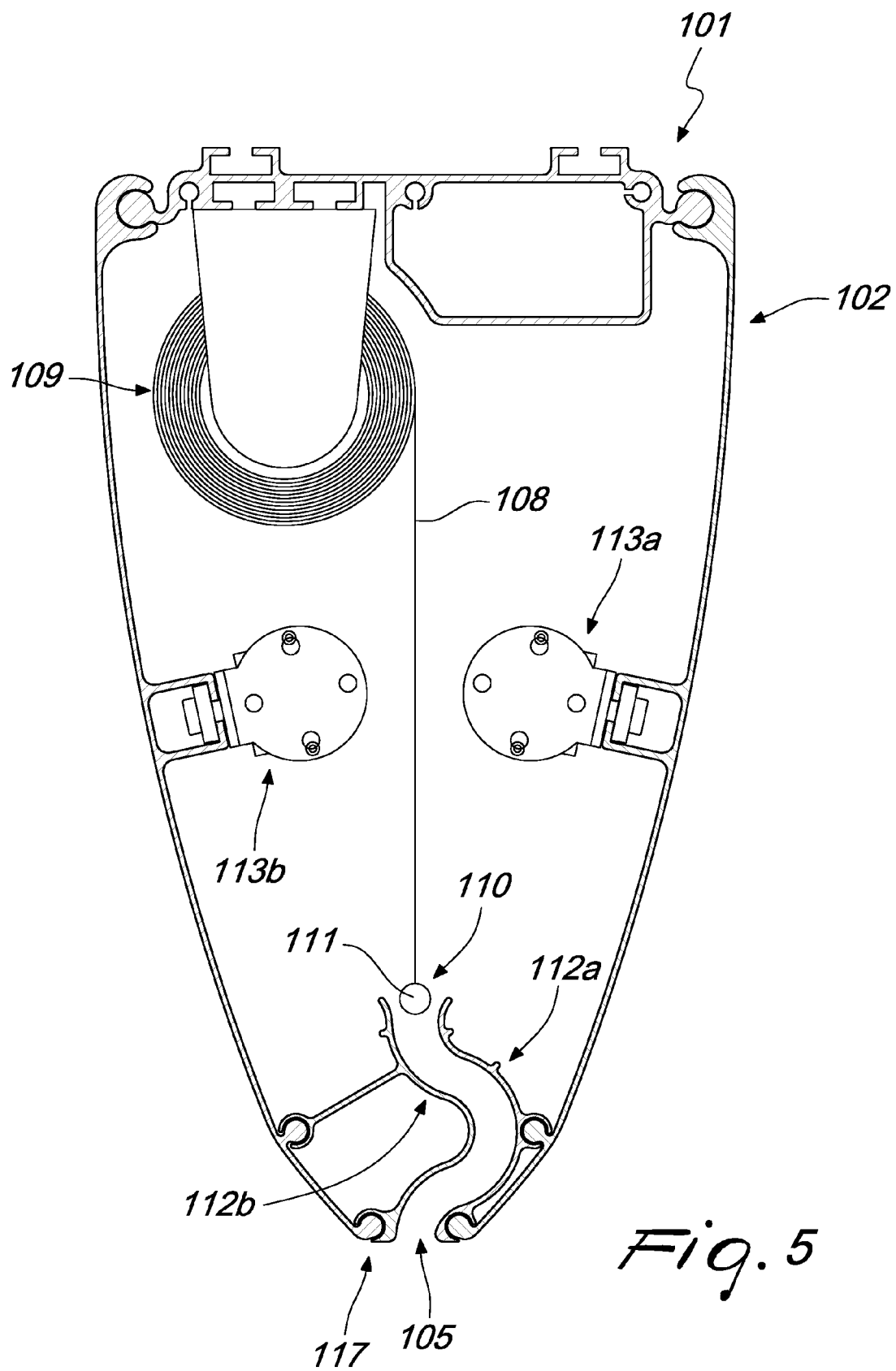
FIG. 5 is a view, similar to that in the previous figure, of a further embodiment of the present invention.

Thus, for example, FIG. 5 shows a solution in which the shade structure 101 is constituted by a horizontal box 102 which is, in a transverse cross-section, teardrop-shaped or triangular with the vertex 117 rounded and directed downwardly. An opening 105 is defined at the vertex 117.

Inside the box 102 a roller 109 is provided, which is motorized and advantageously arranged in a region that lies above and offset with respect to the vertex 117.

The shade 108 is wound around the roller 109 and its end 110 is advantageously associated with a counterweight 111 that acts, inside the box 102, in axial alignment with the opening 105.

Contiguous with the opening 105 a pair of guides 112a, 112b are provided, which are arranged mutually parallel in the direction of the interior of the box 102 so as to define a substantially S-shaped labyrinth through which the shade 108 slides.

The function of the pair of guides 112a, 112b is to guide the correct positioning of the shade 108 at the underlying opening 105 and to prevent the light from emanating outside the box 102.

Arranged inside the box 102 a pair of bactericidal lamps 113a, 113b are provided, which are arranged mutually opposite in a region that is adjacent to the vertex 117 of the box 102.

The characteristics indicated above as advantageous, convenient or similar, may also be missing or be substituted by equivalent characteristics.

The disclosures in Italian Utility Model Application No. TV2013U000035 from which this application claims priority are incorporated herein by reference.

What is claimed is:

1. A shade structure, comprising a horizontal box, said box having an opening arranged in a lower region thereof, said shade structure further comprising a motorized roller arranged inside said box and having shade associated therewith, said shade being arranged to exit from said opening, and said shade structure further comprising at least one bactericidal lamp arranged inside said box for disinfecting said shade inside said box before said shade exits from said opening.

2. The structure according to claim 1, wherein said box, which has a transverse cross-section that is polygonal in plan, has ends open and closeable by way of covers, at a central region of an underside of said box there being arranged said opening that is partially closed by a pair of brushes that are arranged mutually opposite so as to allow the passage between them of said shade.

3. The structure according to claim 1, wherein said shade is wound around said roller and an end thereof is associated with a counterweight, in a region that is adjacent to a plane of arrangement of said shade there being arranged a pair of guides between which said shade is made to slide.

4. The structure according to claim 1, wherein arranged within said box a pair of bactericidal lamps are provided, which are arranged mutually opposite in a region that is adjacent to said opening of said box.

5. The structure according to claim 4, further comprising a pair of guides arranged in said box for guiding said shade between said pair of guides, and wherein said pair of bactericidal lamps is arranged in a region underlying said pair of guides such that said shade is positioned between them in a condition substantially perpendicular to an axis of said pair of lamps.

6. The structure according to claim 4, wherein said pair of bactericidal lamps is of the type with UV-C rays.

7. The structure according to claim 4, wherein said pair of bactericidal lamps is activated together with a motor of said roller while said motor raises and lowers said shade.

8. The structure according to claim 1, wherein on a front surface of said box an on/off indicator and a lapsed time meter are provided.

9. A shade structure, comprising a box, said box having an opening arranged in a lower side thereof, said shade structure further comprising a motorized roller arranged inside said box and having a shade associated therewith, said shade being arranged to exit from said opening, and said shade structure further comprising at least one bactericidal lamp arranged inside said box for disinfecting said shade inside said box before said shade exits from said opening, wherein said box is teardrop-shaped or triangular in transverse cross-section, with a vertex rounded and directed downwardly, said opening being defined at said vertex.

10. The structure according to claim 9, wherein said roller is present within said box, comprises a motor and is arranged in a region that lies above and offset with respect to said pair of brushes or to said vertex, said roller being constituted by a tube and being moved by way of an adapted axial motor, optionally removable.

11. A shade structure, comprising a horizontal box that is open in a lower region and comprises within it a motorized roller with a shade associated therewith, cooperating with optional guides, and at least one bactericidal lamp, wherein said shade is wound around said roller and an end thereof is associated with a counterweight, in a region that is adjacent to a plane of arrangement of said shade there being arranged a pair of guides between which said shade is made to slide, and wherein said guides are arranged mutually parallel in a direction of the interior of said box so as to define a substantially S-shaped labyrinth through which said shade slides, said guides being adapted to guide said shade and to prevent light from emanating from said box.

* * * * *